United States Patent [19]

Arcamone et al.

[11] 4,125,707

[45] Nov. 14, 1978

[54] PROTECTED PSEUDOTRISACCHARIDE INTERMEDIATE FOR PAROMOMYCIN AND NEOMYCIN DERIVATIVES

[75] Inventors: Federico Arcamone, Milan; Giuseppe Cassinelli, Voghera, both of Italy

[73] Assignee: Societa' Farmaceutici Italia S.p.A., Milan, Italy

[21] Appl. No.: 780,232

[22] Filed: Mar. 22, 1977

Related U.S. Application Data

[63] Continuation-in-part of Ser. No. 580,245, May 23, 1975, abandoned.

[30] Foreign Application Priority Data

May 28, 1974 [IT] Italy ................................ 23230 A/74

[51] Int. Cl.² ............................................ C07H 15/22
[52] U.S. Cl. ...................................... 536/17; 424/180; 536/4; 536/12
[58] Field of Search .............................. 536/4, 17, 12

[56] References Cited

U.S. PATENT DOCUMENTS

| | | | |
|---|---|---|---|
| 3,808,198 | 4/1974 | Naito et al. | 536/17 |
| 3,879,375 | 4/1975 | Daniels | 536/4 |
| 3,897,412 | 7/1975 | Naito et al. | 536/17 |

*Primary Examiner*—Johnnie R. Brown
*Attorney, Agent, or Firm*—Stevens, Davis, Miller & Mosher

[57] ABSTRACT

Amino- and oxygen-protected pseudotrisaccharide is disclosed, which has been proved to be a useful intermediate for preparing aminoglycoside antibacterial antibiotics related to paromomycin and neomycin. Process for its preparation is also disclosed.

3 Claims, No Drawings

PROTECTED PSEUDOTRISACCHARIDE INTERMEDIATE FOR PAROMOMYCIN AND NEOMYCIN DERIVATIVES

DESCRIPTION OF THE INVENTION

This application is a continuation-in-part of our copending application Ser. No. 580,245, filed May 23, 1975, now abandoned.

This invention relates to a new protected pseudotrisaccharide, useful as an intermediate for the synthesis of a number of novel aminoglycoside antibacterial antibiotics relates to paromomycin and neomycin.

A particular object of the present invention is an O-, N-protected pseudotrisaccharide having only the 4-hydroxy group available for subsequent glycosylation. It corresponds to the formula (V)

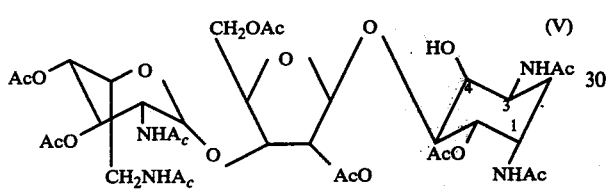

This compound, namely 1,3,6-N,N,O-triacetyl-5-O-[2,5-di-O-acetyl-3-O-(2,6-diacetamido-3,4,-di-O-acetyl-2,6-dideoxy-β-L-idopyranosyl)-β-D-ribofuranosyl]-2-deoxystreptamine, is prepared starting from tetra-(N-1, N-3, N-2''',N-6''')-N-acetyl-paromomycin (I), as described and claimed in U.S. application Ser. No. 565,657, filed Apr. 7, 1975, now U.S. Pat. No. 4,021,601.

More particularly, tetra-(N-1, N-3, N-2''', N-6''')-N-acetylparomomycin (I) is treated with carbobenzoxy chloride to give tetra-(N-1, N-3, N-2''', N-6''')-N-acetyl-mono-N-2'-carbobenzoxyparomomycin (II) which was per-O-acetylated with acetic anhydride in pyridine to give the corresponding octa-O-acetyl derivative (III). Removal of the carbobenzoxy group by catalytic hydrogenation over 10% palladium carbon in acidic methanol gives the corresponding tetra-(N-1, N-3, N-2''', N-6''')-N-acetyl-octa-O-acetylparomomycin (IV) as the hydrochloride.

Deamination of compound (IV) with sodium nitrite in dilute aqueous acetic acid gives the protected pseudotrisaccharide derivative (V) having only the 4-hydroxy group free (Scheme 1).

SCHEME 1

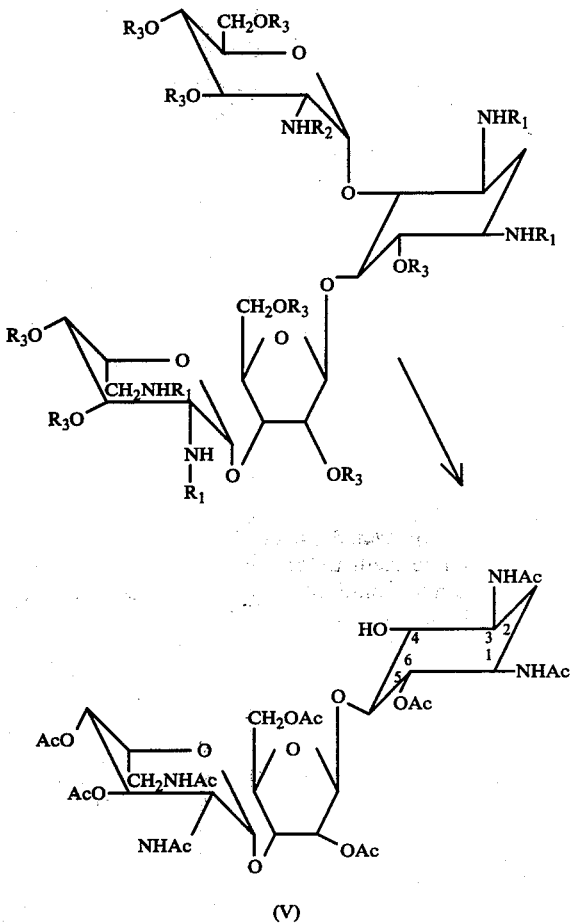

I : $R_1=Ac, R_2=H, R_3=H$

II : $R_1=Ac, R_2=Cbz, R_3=H$ (Cbz=$\overset{O}{\underset{\|}{C}}$—O—CH$_2$—⟨ ⟩)

III : $R_1=Ac, R_2=Cbz, R_3=Ac$

IV : $R_1=Ac, R_2=H, HCl, R_3=Ac.$

The course of the last reaction step can be schematically shown as follows:

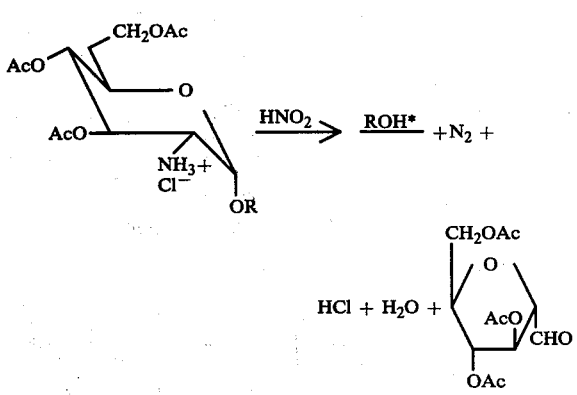

where R=

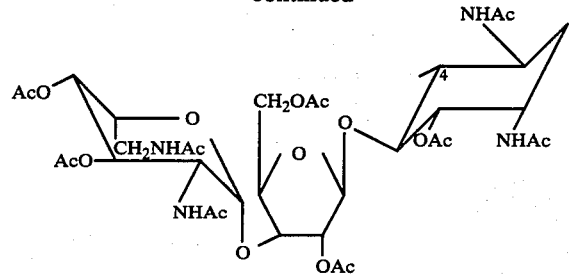

Table 1-continued

| | Antibacterial Activity | | | |
|---|---|---|---|---|
| | MIC µg/ml | | DT$_{50}$ mg/kg(mice) | |
| Strains | 224 | Aminosidine | 224 | Aminosidie |
| E.coli K12 | 125 | 500 | | |
| Proteus sp.1 | 125 | 500 | | |
| Proteus sp.2 | 250 | >500 | | |
| Proteus sp.3 | 125 | >500 | | |
| Proteus sp.4 | 125 | >500 | | |
| Proteus sp.5 | 250 | >500 | | |

Table 2

| | Activity (ID*50%) | | | | | |
|---|---|---|---|---|---|---|
| | Ochromonas malhamensis | Euglena gracilis | Tetrahymena geleei | Entamoeba histolytica | Ribosomes (°) | |
| | (Λ) | (Λ) | (Λ) | (Λ) | 70S | 80S |
| 224 | >100 | >100 | >100 | >20 | 40 | >500 |
| Aminosidine | 1.56 | 12.5 | 12.5 | 1 | 30 | 65 |

(*)Dose inhibiting 50% of growth (Λ) or of protein synthesis(*).

This new protected pseudotrisaccharide (V) can be used as an intermediate for preparing new aminoglycoside antibacterial antibiotics utilizing the Lemieux reaction (R. Lemieux et al., Canad. J. Chem. 51, 53, 1973) with a monosaccharide as the other reagent. For example, 4-0-(6-amino-6-deoxy-α-D-glucopyranosyl)-5-0-[3-0-(2,6-diamino-2,6-dideoxy-β-L-idopyranosyl)-β-D-ribofuranosyl]-2-deoxy-streptamine has been obtained by treatment of compound (V) with the dimer of 3,4-di-0-acetyl-2-deoxy-2-nitroso-6-0-tosyl-α-D-glycopyranosyl chloride (T. L. Nagabhushan, Canad. J. Chem. 48, 257, 1970) as described in Examples 3, 4, 5 below.

4-0-(6-Amino-6-deoxy-α-D-glucopyranosyl)-5-0-[3-0-(2,6-diamino-2,6-dideoxy-β-L-idopyranosyl-β-D-ribofuranosyl]-2-deoxystreptamine (hereinafter referred to as compound 224) is a new aminoglycoside antibacterial antibiotic and it has been tested both "in vitro" and "in vivo" in comparison with aminosidine (paromomycin).

The "in vitro" tests were carried out with the method of serial dilutions in liquid medium (Nutrient Broth Difco). The minimal inhibitory concentration (MIC) was determined after 24 h incubation at 37° C.

The therapeutic activity was assessed in mice experimentally infected with Staphylococcus aureus and treated (4 h after infection) with a single dose of the compound by the subcutaneous route.

Other tests were carried out on algae and protozoa in order to evaluate the sensitivity of eukaryotic organisms to this new molecule (determination of MIC in liquid nutrient medium).

Finally, compound 224 was tested as an inhibitor of protein synthesis on cell-free systems containing ribosomes from Escherichia coli (7OS) or from Saccharomyces cerevisiae (8OS).

The results obtained are reported in Tables 1 and 2.

Table 1

| | Antibacterial Activity | | | |
|---|---|---|---|---|
| | MIC µg/ml | | DT$_{50}$ mg/kg(mice) | |
| Strains | 224 | Aminosidine | 224 | Aminosidie |
| Staphilococcus aureus | 6.2 | 3.1 | 50 | 25 |
| Klebsiella pneumoniae | 2 | 1 | | |
| Escherichia coli B | 12.5 | 6.2 | | |
| E.coli 526 | 100 | >500 | | |

It will be observed (Table 1) that compound 224 exerts a remarkable antibacterial activity in vitro and in vivo on bacteria sensitive to the aminosidine. In addition, it prevents the growth of resistant strains (E. coli, Proteus sp.) at concentrations at which aminosidine proved to be completely inactive.

In Table 2 the results of the tests carried out on eukaryotic microorganisms are given. It will be seen that compound 224 does not affect the growth of algae and protozoa; the opposite is true for aminosidine, a strong inhibitor of the organisms tested.

The different behaviour of the new compound against schizomycetes and eukaryotes is confirmed by the selective inhibition of protein synthesis brought about by 7OS ribosomes, in comparison with 8OS.

There were also carried out comparative trials for determining the actue toxicity and ototoxicity. The LD$_{50}$ values in mice by the subcutaneous route are: Aminosidine, 700 mg/kg; Compound 224, 1000 mg/kg.

As to ototoxicity, the audiometric tests in guinea pigs (Prayer reflex) demonstrated that the audiometric deficit at a given does (340 mg/kg) was lower for compound 224 than for aminosidine by a ratio of 1:2.

It can thus be concluded that compound 224 is a new derivative of aminosidine whose antibacterial activity is of the same order of magnitude of that of aminosidine on sensitive strains, but clearly superior on resistant strains.

The resistance to the aminosidine is due, in the case of E. coli 526, to the production of an aminoglycoside inactivating enzyme (NKT I); the other strains are clinical isolates whose mechanism of resistance is not know.

The following examples will serve to illustrate the invention but without limiting it.

EXAMPLE 1

Tetra(N-1, N-3, N-2''', N-6''')-N-acetyl-octa-0-acetyl-paromonycin chloride (IV)

To a solution of 14.5 g of tetra-(N-1, N-3, N-2''', N-6''')-N-acetyl-paromomycin (I) in 550 ml of water, 460 ml of acetone and 217 g of sodium bicarbonate were added. After cooling to 0° in an ice-salt bath, a solution of 4.6 ml of carbobenzoxy chloride in 90 ml of acetone was added under stirring. The mixture was stirred for 4 hours, and then kept at 0° for 3 days. The solvent was evaporated off, the residue taken up with methanol, and the product precipitated with ethyl ether.

16 g of tetra-(N-1, N-3, N-2''', N-6''')-acetyl-N-2'-carbobenzoxyparomomycin (II), melting at 198°–200° (decomposition) were obtained; $[\alpha]_D^{20°} = +57°$ (c=1, MeOH), Rf = 0.47 (TLC on silica gel, solvent CHCl$_3$:EtOH:H$_2$O, 4:7:2), Rf = 0.57 (CHCl$_3$:MeOH, 1:1).

16 g of this compound, dried in vacuo over P$_2$O$_5$, were dissolved in 160 ml of anhydrous pyridine and treated dropwise, under stirring at 0°, with 12 ml of acetic anhydride. The reaction mixture was kept for 96 hours at room temperature and then put into ice-water, acidified to pH 5 with aqueous acetic acid, and concentrated to 200 ml. From this solution, 13.2 g of white crystals of tetra-(N-1, N-3, N-2''', N-6''')-N-acetyl-N-2'-carbobenzoxy-octa-0-acetylparomomycin (III), m.p. 269°–271° C, $[\alpha]_D^{20°} = +56°$ (c = 1, MeOH), precipitated at 0° C. From the mother liquor a further 2.24 g were obtained.

A solution of 14.5 g of this compound, in 1000 ml of methanol containing 11.1 ml of N-hydrochloric acid, was hydrogenated at room temperature and atmospheric pressure, using 10% palladium on carbon as a catalyst. During the reaction the pH value was maintained neutral by adding HCl in methanol.

The catalyst was then filtered off, the solution concentrated in vacuo, and 13.2 g of the title compound (IV) was precipitated with ether : m.p. 200°–205° C, $[\alpha]_D^{20°} = +63°$ (c = 1, MeOH).

EXAMPLE 2

1,3,6-N,N,O-triacetyl-5-0-[2,5-O-acetyl-3-0-(2,6-diacetamido-3,4-di-O-acetyl-2,6-dideoxy-β-L-idopyranosyl)-β-D-ribofuranosyl]-2-deoxystreptamine (V)

A solution of 12.5 g of the compound (IV), obtained as described in the previous example, in 85 ml of water was cooled to 0° C, and treated, under stirring, with 47.5 ml of 10% aqueous acetic acid and with 2.70 g of sodium nitrite, meanwhile maintaining the pH value between 3 and 4. The reaction mixture was stirred at 0° C for 1 hour, subjected to a nitrogen current in order to eliminate the nitrous vapors, and then lyophilized.

The solid was dissolved in a chloroform:methanol:water mixture (150:42:6) and chromatographed on a silica gel column, using the above mixture as eluent. The solvent was evaporated off, the residue taken up with methanol and the solution was treated with an excess of ethyl ether to give 4.85 g of compound (V), m.p. 157°–160° (dec.), $[\alpha]_D^{20°} = +17°$ (c = 1, CHCl$_3$), Rf 0.45 (TLC on silica gel, solvent CHCl$_3$:MeOH:HO$_2$O 150:42:6).

EXAMPLE 3

1,3,6-N,N,O-triacetyl-4,0-(3,4-di-0-acetyl-2-oximino--6-0-tosyl-α-D-arabinoesopyranosyl)-5-0-[2,5-di-0-acetyl-3-0-(2,6-diacetamido-3,4-0-di-acetyl-2,6-dideoxy-β-L-idopyranosyl)-β-D-ribofuranosyl]-2-deoxystreptamine A solution of 9.4 g of the compound obtained in Example 2, in 31 ml of anhydrous dimethylformamide, was treated with 7.1 g of the dimer of 3,4-di-0-acetyl-2-deoxy-2-nitroso-6-0-tosyl-α-D-glucopyranosyl chloride, prepared according to T. L. Nagabhushan, Canad. J. Chem. 48, 257, 1970, and the mixture was stirred for 50 hours at room temperature. Upon adding 600 ml of ether, a solid was obtained which was taken up with methylene chloride and precipitated with ether in excess. This material (13.5 g) was chromatographed on a silica-gel column (500 g) using chloroform and methanol as eluent.

The fractions containing 7% methanol were collected and the solvent evaporated off : 7.34 g of the product melting at 152°–153° C (decomposition) were obtained; $[\alpha]_D^{20°} = +18°$ (c = 0.5, CHCl$_3$).

EXAMPLE 4

1,3,6-N,N,O-triacetyl-4-0-(2,3,4-tri-O-acetyl-6-0-tosyl--α-D-glucopyranosyl)-5-0-[2,5-di-0:acetyl-3-0-(2,6-diacetamido-3,4-di-0-acetyl-2,6-dideoxy-β-L-idopyranosyl)-β-D-ribofuranosyl]-2-deoxystreptamine.

A solution of 3 g of the compound of Example 3, in 18.4 ml of acetonitrile, was treated with 1.84 ml of N aqueous hydrochloric acid and with 3.7 ml of acetaldehyde and stirred at room temperature.

After 5 hours, the excess of acetaldehyde was eliminated in vacuo, the mixture diluted with 50 ml of methylene chloride, and washed with a 1% aqueous solution of sodium bicarbonate. The organic phase was separated, dried on sodium sulphate, and evaporated in vacuo.

The residue (2.75 g) was poured into a mixture of 42 ml of dioxane and 8.5 ml of water and treated (under stirring and cooling at 0° C) with 690 mg of sodium borohydride. The solution was neutralized with a sulphonic exchange-resin (acid form), the resin was filtered off, and the solution evaporated to dryness.

The residue (1.8 g) was dissolved in 30 ml of anhydrous pyridine, treated with 20 ml of acetic anhydride, and maintained for 16 hours at room temperature. The excess of acetic anhydride was decomposed with water and ice, and 1.9 g of the title compound melting at 171°–172° C were obtained by lyophilization of reaction mixture.

EXAMPLE 5

4-0-(6-amino-6-deoxy-α-D-glucopyranosyl)-5-0-[3-0-(2,6-diamino-2,6-dideoxy-β-L-idopyranosyl)-β-D-ribofuranosyl]-2-deoxy-streptamine.

A solution of 1 g of the compound obtained in Example 4, in 30 ml of anhydrous dimethylformamide, was treated with 1.1 g of sodium azide and heated under stirring for 7 hours at 100° C.

The solution was then cooled, filtered and evaporated in vacuo. The residue, dissolved in 100 ml of methanol, was combined with 1.25 ml of N hydrochloric acid and hydrogenated at room temperature and atomspheric pressure on 10% palladium carbon as catalyst.

Then the catalyst was filtered, the solution neutralized with sodium hydroxide, methanol evaporated off, and 2.5 ml of 50% sodium hydroxide were added, followed by heating for 6 hours at 135° C.

After cooling, the pH was adjusted to 10.5 with 6 N aqueous sulphuric acid and the solution extracted twice with 20 ml of n-butyl alcohol containing 2.5 ml of benzaldehyde. From the extracts, the desired product was obtained by extraction with dilute aqueous sulphuric acid.

The aqueous phase was separated and the title compound was obtained as free base by treatment with an anionic exchange-resin (base form). By lyophilization 0.22 g of product were obtained; m.p. 190° C (decomposition), $[\alpha]_D^{20°} = +46°$ (c = 0.5, H$_2$O).

What is claimed is:

1. 1,3,6,-N,N,O-triacetyl-5-0-[2,5-di-0-acetyl-3-0-(2,6-diacetamido-3,4-di-0-acetyl-2,6-dideoxy-β-L-idopyranosyl)-β-D-ribofuranosyl]-2-deoxystreptamine.

2. 4-0-(6-amino-6-deoxy-α-D-glucopyranosyl)-5-0-[3-0-(2,6-diamino-2,6-dideoxy-β-L-idopyranosyl)-β-D-ribofuranosyl]-2-deoxy-streptamine.

3. A process for preparing the compound 1,3,6-N,N,O-triacetyl-5-0-[2,5-di-0-acetyl-3-0-(2,6-diacetamido-3,4-di-0-acetyl-2,6-dideoxy-β-L-idopyranosyl)-β-D-ribofuranosyl]-2-deoxystreptamine, which comprises treating tetra-(N-1, N-3, N-2''', N-6''')-N-acetyl-mono-N-2'-carbobenzoxyparomomycin, per-0-acetylating with acetic anhydride in pyridine to give the corresponding octa-0-acetyl derivative, removing the carbobenzoxy group by catalytic hydrogenation over 10% palladium carbon in acidic methanol to give tetra-(N-1, N-3, N-2''', N-6''')N-acetyl-octa-0-acetyl-paromomycin, deaminating with sodium nitrite in dulute aqueous acetic acid to obtain as a result of a concerted reaction the ring contraction of the 0-acetyl-D-glucosaminyl moiety and the concommitant cleavage of the glycosidic linkage between the 0-acetyl-D-glucosaminyl and 2-deoxystreptamine moieties, the desired 1,3,6-N,N,O-triacetyl-5-0-[2,5-di-0-acetyl-3-0-(2,6-diacetamido-3,4-di-0-acetyl-2,6-dideoxy-β-L-idopyranosyl)-β-D-ribofuranosyl]-2-deoxystreptamine.

* * * * *

UNITED STATES PATENT AND TRADEMARK OFFICE
CERTIFICATE OF CORRECTION

PATENT NO. : 4,125,707
DATED : November 14, 1978
INVENTOR(S) : Federico Arcamone et al It is certified that error appears in the above–identified patent and that said Letters Patent are hereby corrected as shown below:

Column 1, formula (V) should read as follows:

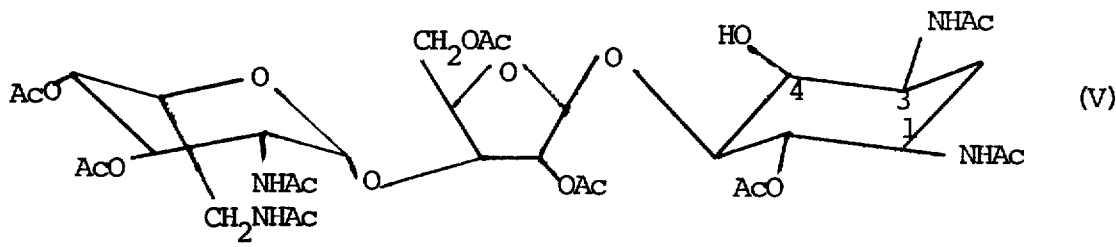

Column 4, Example 1, line 60, "paromonycin chloride" should read --paromomycin hydrochloride--.

*Signed and Sealed this*

*Thirtieth* Day of *October 1979*

[SEAL]

*Attest:*

RUTH C. MASON
*Attesting Officer*

LUTRELLE F. PARKER
*Acting Commissioner of Patents and Trademarks*